(12) United States Patent
Van Andel

(10) Patent No.: US 11,037,369 B2
(45) Date of Patent: Jun. 15, 2021

(54) VIRTUAL OR AUGMENTED REALITY REHABILITATION

(71) Applicant: Zimmer US, Inc., Warsaw, IN (US)

(72) Inventor: Dave Van Andel, Spring Lake, MI (US)

(73) Assignee: Zimmer US, Inc., Warsaw, IN (US)

( * ) Notice: Subject to any disclaimer, the term of this patent is extended or adjusted under 35 U.S.C. 154(b) by 80 days.

(21) Appl. No.: 15/966,491

(22) Filed: Apr. 30, 2018

(65) Prior Publication Data

US 2018/0315247 A1 Nov. 1, 2018

Related U.S. Application Data

(60) Provisional application No. 62/492,667, filed on May 1, 2017.

(51) Int. Cl.
| | |
|---|---|
| *G06T 19/00* | (2011.01) |
| *G16H 20/30* | (2018.01) |
| *G06F 3/01* | (2006.01) |
| *G06K 9/62* | (2006.01) |
| *G06K 9/00* | (2006.01) |
| *G16H 50/30* | (2018.01) |
| *G16H 50/20* | (2018.01) |
| *G16H 40/63* | (2018.01) |

(52) U.S. Cl.
CPC ............ *G06T 19/006* (2013.01); *G06F 3/016* (2013.01); *G06K 9/00335* (2013.01); *G06K 9/00342* (2013.01); *G06K 9/00671* (2013.01); *G06K 9/6267* (2013.01); *G16H 20/30* (2018.01); *G16H 40/63* (2018.01); *G16H 50/20* (2018.01); *G16H 50/30* (2018.01)

(58) Field of Classification Search
CPC ...... G06T 19/006; G16H 50/20; G16H 50/30; G16H 40/63; G16H 20/30; G06K 9/00342; G06K 9/00671; G06K 9/00335; G06F 3/016
See application file for complete search history.

(56) References Cited

U.S. PATENT DOCUMENTS

| | | | |
|---|---|---|---|
| 2011/0230792 A1* | 9/2011 | Sarig-Bahat | A61B 5/1124 600/595 |
| 2014/0228985 A1* | 8/2014 | Elliott | A63B 71/06 700/91 |
| 2016/0129343 A1* | 5/2016 | Domansky | A63F 13/21 463/7 |
| 2016/0249008 A1* | 8/2016 | Kitazawa | G02B 27/017 |
| 2016/0338644 A1* | 11/2016 | Connor | A61B 5/4528 |
| 2017/0061817 A1* | 3/2017 | Mettler May | G09B 19/003 |
| 2017/0312031 A1 | 11/2017 | Amanatullah et al. | |
| 2017/0312032 A1 | 11/2017 | Amanatullah et al. | |

(Continued)

*Primary Examiner* — Kee M Tung
*Assistant Examiner* — Khoa Vu
(74) *Attorney, Agent, or Firm* — Schwegman Lundberg & Woessner, P.A.

(57) ABSTRACT

A system and method may be used to assess range of motion of a target body part. A method may include comparing reference range of motion capabilities of a body part that mirrors or matches the target body part (e.g., from a camera or a database) to captured range of motion capabilities of the target body part. The comparison may result in an assessment, a virtual animation, a virtual component, or other output, such as to be displayed on a display or an augmented reality display.

17 Claims, 11 Drawing Sheets

(56) References Cited

U.S. PATENT DOCUMENTS

2018/0070864 A1\* 3/2018 Schuster .............. A61B 5/0077
2018/0096615 A1\* 4/2018 Tanaka ............... G06K 9/00355
2020/0016363 A1\* 1/2020 Macri ................... A61M 21/00

\* cited by examiner

VIRTUAL OR AUGMENTED REALITY REHABILITATION

CLAIM OF PRIORITY

This application claims the benefit of priority to U.S. Provisional Application Ser. No. 62/492,667, filed May 1, 2017, titled "Virtual or Augmented Reality Rehabilitation," which is hereby incorporated herein by reference in its entirety.

TECHNICAL FIELD

The disclosure generally relates to using a computer system to assess a patient's limb mobility and range of motion in three dimensions and determine a patient program for limb movement improvement.

BACKGROUND

Through different activities such as sports, occupational exertions, or day to day movements, a person may experience difficulty with the movement of their limbs and joints. These movement issues may cause pain and lead to problems with mobility, stability, and range of motion. Treatment of these limb problems may involve surgery or a physical therapy program, where a patient is instructed to perform a movement meant to stretch and strengthen the muscles in the affected area. Typically, the instructions given to a patient are verbal or included on a printed piece of paper, which may be forgotten or lost by the patient. Evaluating a patient for surgery or physical therapy also usually requires an office visit, which may be time consuming and inconvenient for the patient and the clinician.

A person may also wish to increase or improve technique or range of motion for a sports-related movement, such as a when swinging a golf club. Similar issues arise for receiving instructions related to sports movements as those described above for the patient. Further, finding a qualified trainer may be difficult.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
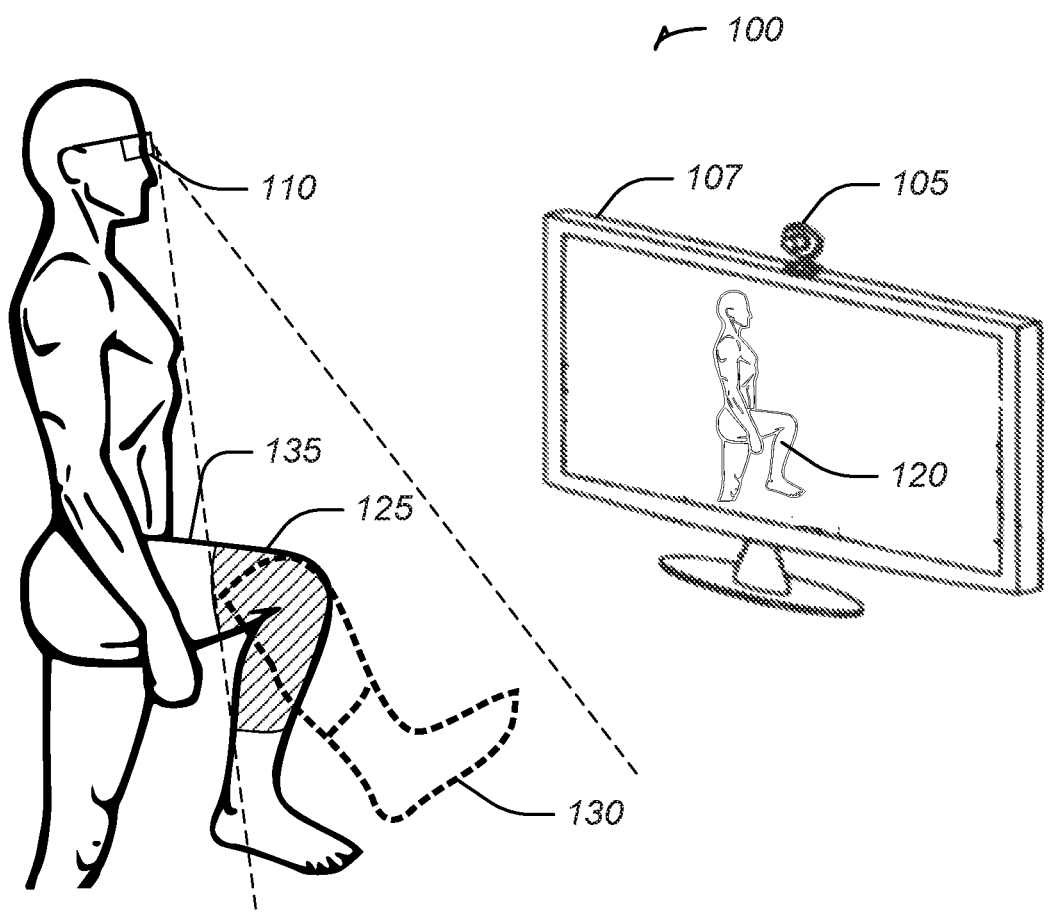
FIG. 1A and FIG. 1B illustrate real and virtual aspects of an augmented reality diagnosis system in accordance with some embodiments.

In general, this disclosure describes techniques that may allow a computer system equipped with cameras and sensors to assess a patient's mobility and stability three-dimensionally. The system may capture three-dimensional data about the of a target body part on a person, such as an arm or leg and including the movement of joints such as the elbow or knee. The gathered data may then be analyzed by a remote clinician or an artificial intelligence system to determine the patient's range of motion and motor control. The three-dimensional data may then be analyzed by a clinician or artificial intelligence system against norms to determine a patient assessment. The assessment may then be a program to immerse the patient in three-dimensional tasks and challenges aimed at provoking the thresholds of the patient's measured mobility and stability.

The systems and methods herein describe using a movement capture apparatus, such as a camera or an infrared (IR) detection device, to capture movement information from a patient. The systems and methods may be used for remote diagnosis or feedback. In an example, a system may provide a user interface, a video display, an augmented reality (AR) display, a virtual reality (VR) display, audible alerts, haptic feedback, a non-contact alert, or the like to present feedback.

In an example, a system may be used to remotely or locally diagnose a limb mobility problem for a patient. For example, a remote clinician or an artificial intelligence system (e.g., a machine learning system trained to detect limb mobility problems) may be used to diagnose an issue. The system may provide feedback to the patient, such as an assessment, a recommended physical therapy technique, surgery, a consultation, etc. The system may capture movement of a target body part, such as the limb. Data collected from the captured movement may then be compared to a reference set, for example including range of motion capabilities of the limb (e.g., based on patient specific data, such as height, gender, etc.). The reference set may be gathered by capturing similar movements performed by the patient's mirroring target body part (e.g., when the patient is having an issue with a right leg, then a reference set of data may be collected from capturing movement of the patient's left leg). The reference set may include compiled data collected from other people who share traits similar to the patient, such as gender, weight, or height. In another example, the reference set may include data created using machine learning techniques, based on clinical data, or based on a machine-determined range of motion. A machine learning system may generate ideal or optimized data for the reference set based on patient specific parameters, such as hip to knee measurement, knee to ankle measurement, etc. The comparison between the patient's data and the reference set may determine a difference set. An assessment for the patient may then be determined based on the difference set. The assessment may be determined by an analysis performed by a clinician or a process performed by an artificial intelligence system. The assessment is then output to the patient. The output may include a physical therapy program for the patient to perform immediately or over a prescribed period of time. The output may include a recommendation for the patient to visit a doctor as the target body part may require surgery or other medical procedure.

The assessment provided to the patient may include a physical therapy program including various movements or stretches the patient is to perform with the target body part. The system used to capture the movements of the target body part for diagnosis may be used to assist in guiding the patient through the therapy routines.

The captured movement of the target body part creates the measurement set. The measurement set includes of three-dimensional data points for the movement performed by the target body part. The three-dimensional data points may be captured with video using a movement capture apparatus such as a camera or a Kinect from Microsoft of Redmond, Wash. The patient may have one or more sensors attached to the target body part, which may supply information about the movement of the target body part or its position in three-dimensional space. The one or more sensors may be attached directly to the patient or may be part of a worn apparatus such as a sleeve the patient places around an arm or leg. The one or more sensors may include one or more of an accelerometer, a magnetometer, a gyroscope, an optical sensor, an ultrasonic sensor, an inertial measurement unit, a multi-axis sensor, or a contact pressure sensor. In an example, a patent may wear a sleeve that extends from an upper thigh to a lower calf. The sleeve may have one or more sensors located above the knee or below the knee such that the one or more sensors may collect data about the movement of the patient's knee joint.

The patient may be directed to perform one or more movements with the target body part (e.g., bending of the knee, raising and lowering an extended leg, extending an arm in a certain direction, etc.). These movements are captured to collect the three-dimensional data points which comprise the measurement set. The movements of the target body part may be performed in a certain manner for the collected three-dimensional data points to accurately portray the movement capabilities of the target body part and be relatively comparable to the reference set data. The system may guide the patient through the steps for proper motion by utilizing augmented reality.

Augmented reality (AR) is a technology for displaying virtual or "augmented" objects or visual effects overlaid on a real environment. The real environment may include a room or specific area, or may be more general to include the world at large. The virtual aspects overlaid on the real environment may be represented as anchored or in a set position relative to one or more aspects of the real environment. For example, a virtual object may be configured to appear to be resting on a table. An AR system may present virtual aspects that are fixed to a real object without regard to a perspective of a viewer or viewers of the AR system. For example, a virtual object may exist in a room, visible to a viewer of the AR system within the room and not visible to a viewer of the AR system outside the room. The virtual object in the room may be displayed to the viewer outside the room when the viewer enters the room. In this example, the room may act as a real object that the virtual object is fixed to in the AR system.

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see a virtual object presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the virtual object (e.g., using one or more cameras), and causing the virtual object to move in response. Virtual aspects may include virtual representations of real world objects or may include visual effects, such as lighting effects, among other things. The AR system may include rules to govern the behavior of virtual objects, such as subjecting a virtual object to gravity or friction, or may include other predefined rules that defy real world physical constraints (e.g., floating objects, perpetual motion, etc.).

Systems and methods for using augmented reality (AR) to remotely instruct and guide a patient through movements of a target body part, as well as guide the patient with therapy routines, are described herein. The systems and methods herein describe using AR to display a virtual representation of a patient's limb to illustrate to the patient how to complete a clinical movement. In an example, the AR may be used to display directions for a patient to perform a clinical movement. The real therapist may, for example, be a live therapist appearing with a patient, or may be a video recording of a therapist. The real therapist may be defined as any therapist that is not virtual.

In addition to guiding a patient through movements with a video screen or AR system, a haptic feedback system may be used as part of a worn item such as a sleeve, glove, or sock. Haptic feedback is a technology that recreates the sense of touch or causes a sensation for a user through the use of vibrations or force. An example of the use of haptic feedback includes using a glove worn by a user to produce vibrations felt by the user, the vibrations to indicate that a simulated object is grasped. In an example, the patient, utilizing both AR and a haptic feedback glove, may be instructed to reach for an object positioned within the AR environment that will require the patient to move an arm in a prescribed manner. When the patient "touches" the virtual object (e.g., occupies space in the real environment where the virtual object is projected virtually), a haptic feedback vibration may be produced in the glove to indicate the virtual object is being "touched." In an example, haptic feedback may be used to indicate that the patient has completed a prescribed movement.

The systems and techniques described herein, may be utilized in a pharmacy, an urgent care center, or a walk-in clinic. In an example, the system may be presented as a kiosk with a screen that prompts a patient for information and then guides the patient through prescribed motions for a diagnosis. The kiosk may include a camera, AR glasses, a sleeve, glove, or the like, as described above, such as for capturing or providing feedback based on the patient's movements.

Upon completion of the prescribed motions, the collected data may be transmitted to a clinician or artificial intelligence system for analysis to determine an assessment. The patient may receive the assessment while at the kiosk, may be asked to return to the kiosk at a later point in time to receive the assessment, or may receive the assessment using a different communication protocol (e.g., email). The patient may receive an assessment through electronic communications such as an email, text message, or personalized web page. The assessment may recommend that the patient visit a doctor or physical therapist. The assessment may include an exercise or a physical therapy program. The assessment may recommend to the patient to return to the kiosk (or any similar kiosk) to perform a therapy program. The patient may be presented with an option of performing the therapy program at home, for example by utilizing a personal AR device, a smartphone with camera, a video capture device such as a Kinect from Microsoft of Redmond, Wash., or the like.

Figure 1B:
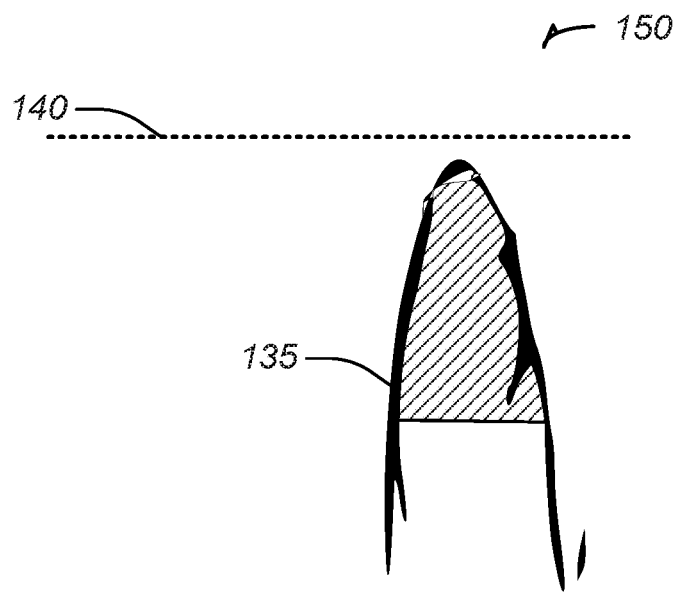

FIG. 1A and FIG. 1B illustrate real and virtual aspects of an augmented reality diagnosis system in accordance with some embodiments. In an example, the system 100 includes a video capture device 105, a display device 107, and AR glasses 110 worn by a user 115. The display device 107 may display an avatar 120 to demonstrate the movements the user 115 should perform. In an example, the avatar 120 is demonstrating the movement of lifting the right leg with the knee bent at a 90 degree angle. The demonstrated bent knee movement is also being performed by the user 115. The user 115 may perform a movement, as instructed, which is captured by the video capture device 105. In an example, a movement may be performed by the user 115 with one or more target body parts, and the movements may be captured by the video capture device 105. In an example, the video capture device 105 may be a camera, a depth camera, or an infrared detection device, such as the Kinect from Microsoft of Redmond, Wash.

In an example, the system 100 may be calibrated using the video capture device 105. The video capture device 105 may use infrared light to detect the user 115 in a field of view. The system 100 may evaluate the detection (e.g., captured images) of the user 115 to identify joints, limbs, appendages, a head, etc., of the user 115. These identified body parts may be used with later captured video of an exercise to label specific body parts.

The system 100 may be used to capture three-dimensional movement. For example, the video capture device 105 may include a movement capture apparatus. The movement capture apparatus may include two or more infrared sensors or cameras to detect or capture three-dimensional movement. The two or more cameras can triangulate positions of the user 115 or identified portions of the user 115 moving within a three-dimensional space. The video capture device 105 may include a camera to capture video in conjunction with infrared captured movement.

In the example, the user 115 in system 100 may wear an apparatus to capture the motion of the target body part. In an example, a leg sleeve 125 is worn on the right leg in the area of the knee for user 115. The worn apparatus may be any type of apparatus that may be secured to a user's body and allow movement (e.g., a sleeve, glove, sock, or wristband). The worn apparatus may contain a sensor for tracking or capturing the movement of the user 115 or the target body part. The sensor utilized may include one or more of an accelerometer, a magnetometer, a gyroscope, an optical sensor, an ultrasonic sensor, an inertial measurement unit, a nine-axis sensor, a contact pressure sensor, or the like.

In system 100, the user 115 may wear the AR glasses 110. In an example, view 150 may represent a view the user 115 sees while wearing the AR glasses 110. The view 150 may include virtual and real aspects in an environment, such as the user's leg (real) augmented by a guide (virtual). In an example, the user 115 may look downward to observe the view 150 and the user may see the raised leg 135 with bent knee. The view 150 using the AR glasses 110 may include a virtual object or goal for the target body part to reach or extend to, such as a virtual line 140. The virtual line 140 may represent an extension distance for the target body part to achieve during a movement. The AR glasses 110 may display virtual aspects in a real environment, such as in view 150.

The user 115 may observe a virtual limb 130 through the AR glasses 110. The virtual limb 130 may demonstrate to the user 115 how to perform a movement or may act as a guide for the user 115 to move the raised leg 135, for example, along a path, or at an extension distance.

Figure 2:
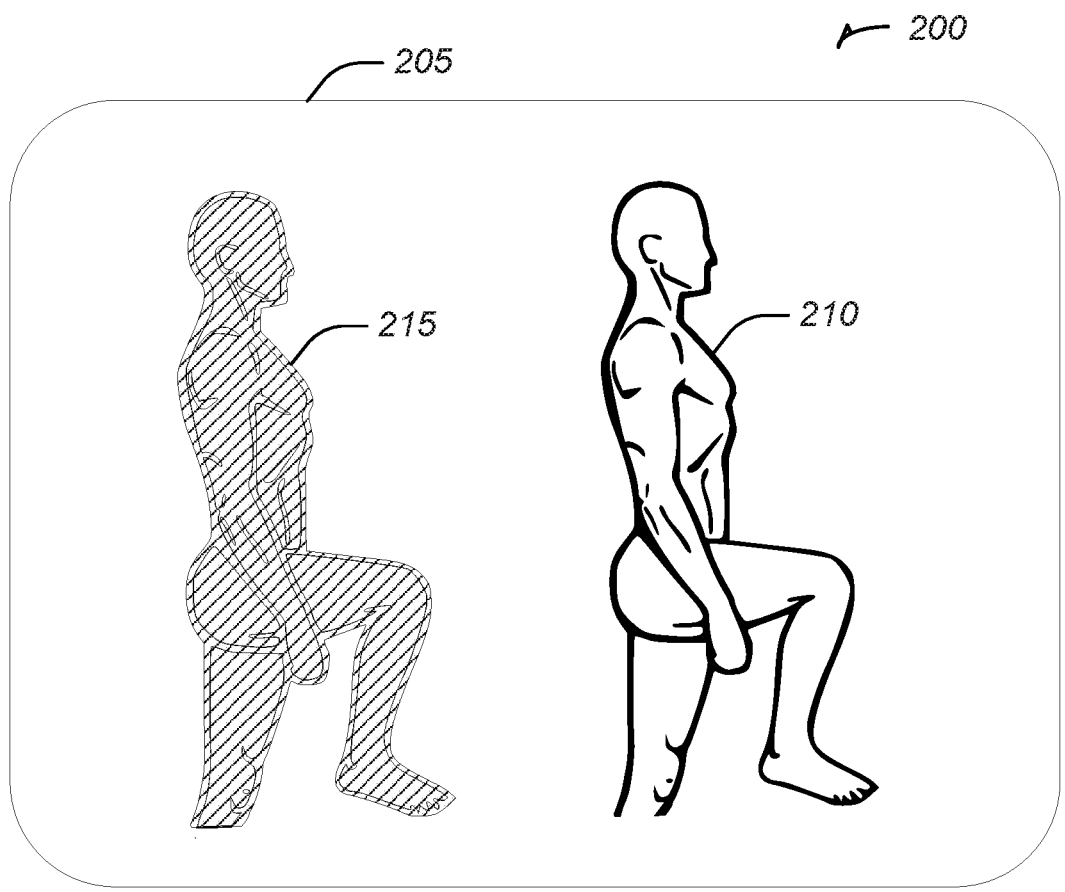
FIG. 2 illustrates an example of a guidance display system in accordance with some embodiments.
Figure 2:
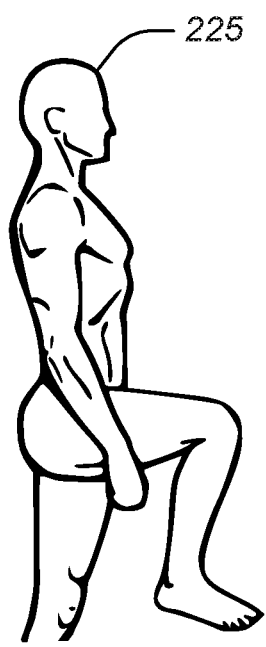

FIG. 2 illustrates an example of a guidance display system 200 in accordance with some embodiments. Captured movements of a user (e.g., using the system 100 of FIG. 1) may be used to collect three-dimensional data points of the movement of a target body part to create the measurement set. A video capture device may be used to capture a user 225 and the movement performed by the user 225. In an example, a display screen 205 presents captured video (e.g., video captured of the movement performed by the user 225 or of the user 225). A virtual guide avatar 215 may be presented on the display screen 205. The virtual guide avatar 215 may be a computer generated figure, an animated figure, or a recording of a human instructor. The virtual guide avatar 215 may instruct the user 225 through a movement to perform (e.g., a speed of movement, where to extend a limb, how far to bend a joint, etc.). The movement may be used to collect movement set data points. The display screen 205 may display a real-time representation 210 of the user 225, for example using the real time captured video of the user 225. The user 225 may view display screen 205 with the displayed captured video of the user 225 to ensure the user movements are properly matching the movements of the virtual guide avatar 215. The display screen 205 may display one or both of the captured video of the user 225, the virtual guide avatar 215, or the real-time representation 210. The real-time representation 210 may be overlaid on the virtual guide avatar 215 (or vice versa) such that the user 225 may control the real-time representation 210 to attempt to match movements of the virtual guide avatar 215. The virtual guide avatar 215 may be displayed with a degree of transparency (e.g., 50% transparent, 30% transparent, 90% transparent, etc.). In an example, to help the user 225 mimic the movements of the virtual guide avatar 215, the real-time representation 210 of the user 225 may be placed over the virtual guide avatar 215.

Figure 3A:
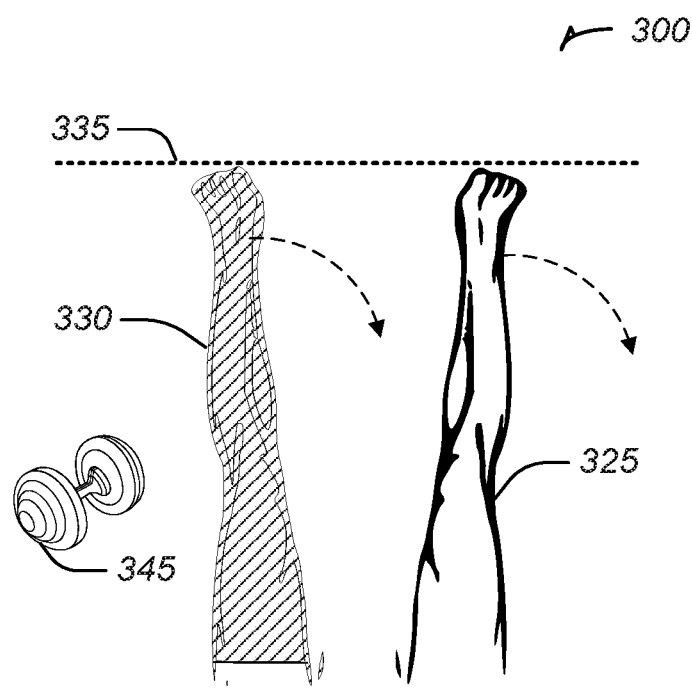
FIG. 3A and FIG. 3B illustrate real and virtual aspects of an augmented reality diagnosis and therapy system in accordance with some embodiments.
Figure 3B:
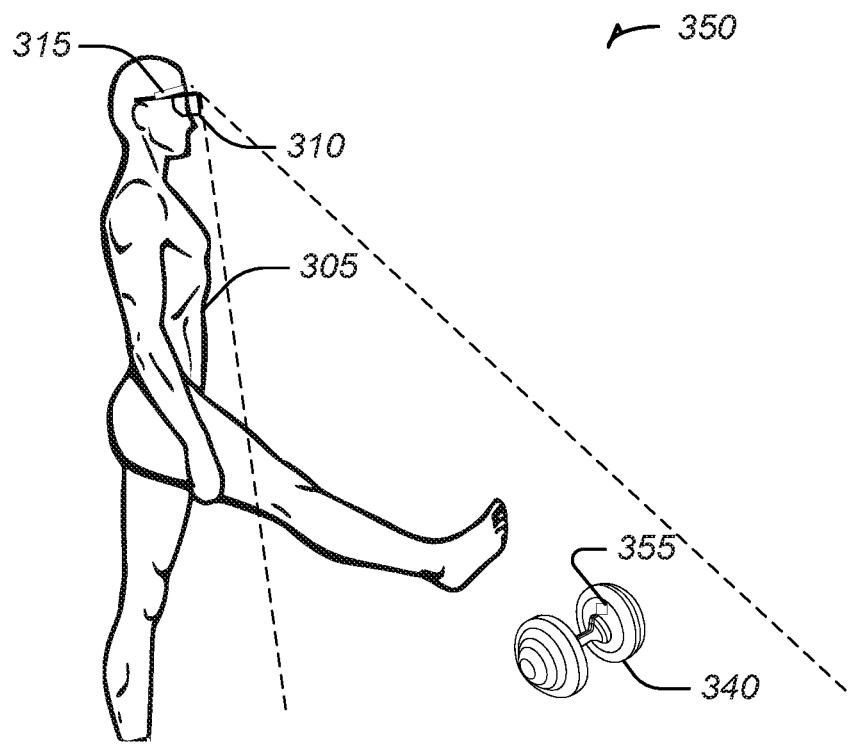

FIG. 3A and FIG. 3B illustrate real and virtual aspects of an augmented reality diagnosis and therapy system in accordance with some embodiments. Within the environment 350, a user 305 may wear an AR device 310. The user 305 may use the AR device 310 to guide the user 305 through movements for a target body part of the user 305. In an example, view 300 may represent a view seen by the user 305 looking through the AR device 310. View 300 includes a combination of real and virtual aspects, such as the user's leg 325 (real) and a virtual guide limb 330 (virtual). The user 315 may see a target body part, such as the right leg 325 of the user 305 through the AR device 310. The view 300 may include a virtual guide target body part, such as the virtual guide limb 330. The virtual guide limb 330 may include a computer generated limb, an animated limb, a visual recording of a human instructor's limb, a visual recording of a mirror limb of the user 305 (e.g., if the leg 325 is the right leg of the user, the virtual guide limb 330 may be a recording of the user's left leg, which may be further modified digitally or augmented), or the like. The view 300 may include a guide line 335 to demonstrate to the user 305 how far the limb is to be extended or other movement criteria.

The AR device 310 may include a camera 315. The camera 315 may include an infrared filter, a visible light filter, a plurality of cameras, a depth camera, etc. The AR device 310 may project virtual items over a representation of a real environment, which may be viewed by the user 305. In an example, the real environment may be permitted to be viewed through the AR device 310 including physical objects, such as a floor, a room, or physical props, among other things. In an example, virtual objects may be displayed using the AR device 310, such as highlighting of a body part, a movement arrow, blurring to show motion, or the like. The virtual guide limb 330 may be placed in the real environment at a predetermined location, such as a location in the real environment that is within an area visible to the user 305 using the AR device 310. For example, the virtual guide limb 330 may located in front of the AR device 310 within the augmented reality environment and visible by the user 305. In an example, when the user 305 turns the AR device 310, the virtual guide limb 330 may be designed to disappear from view similar to how a real limb would disappear when the user's 305 head turned.

In an example, the virtual guide limb 330 may be shown overlaid on the real environment, to demonstrate an exercise. In an example, a virtual display of props or objects, such as for use in exercise may be overlaid on the real environment. For example, virtual object 345 may represent physical object 340. The AR device 310 may be used to instruct the user 305 to find the physical object 340 in the room by displaying the virtual object 345 In an example. In an example, the virtual object 345 may be displayed in use by a virtual instructor.

The physical object 340 may include a sensor 355. The sensor 355 may be used to track patient progress, such as a duration or number of repetitions completed by the user 305. In an example, the sensor 355 may be used to identify the physical object 340 to the AR device 310. Once identified, the AR device 310 may select the virtual object 345 that corresponds to the physical object 340. For example, if the user 305 has a ten pound weight and a five pound weight available, these may be identified via sensors in the weights, and the AR device 310 may determine the five pound weight is to be used in an exercise, and the virtual object 345 may resemble the five pound weight. The virtual object 345 may change to resemble the ten pound weight in another exercise or when increasing weight to increase difficulty for the exercise. In an example, the AR device 310 may display a virtual movement of a limb.

The view 300 may allow the user 305 or a remote user, such as a clinician, to select a joint or location on an AR avatar. By selecting a joint or location on the AR avatar, the user 305 or remote user may indicate what hurts or needs attention on the user 305, select a side of the body, be prompted for a pain level, or the like. In another example, the user 305 may select options from a user interface within the view 300, such as a scale bar to select pain. The view 300 may include a questionnaire for the patient to answer so that a therapist may evaluate progress or determine exercises for the patient.

Figure 4A:
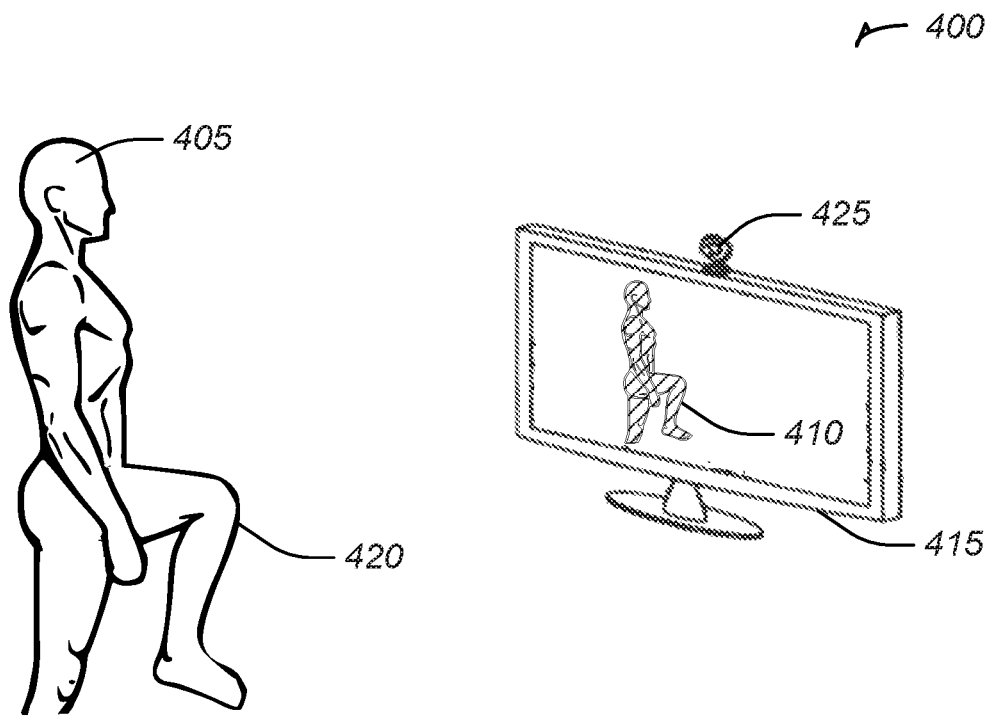
FIG. 4A and FIG. 4B illustrate examples of a patient evaluation system in accordance with some embodiments.

FIG. 4A illustrates a patient evaluation system 400 in accordance with some embodiments. The systems and techniques described herein may use a reference set and a movement set to determine a difference set, which is then used to determine an assessment for a target body part. In an example, a patient may identify a target body part for therapy (e.g., the target body part is causing pain to the patient, the target body part is causing the patient to have difficulty walking, the patient has stiffness with the target body part, etc.). In an example, the system may utilize a reference set, wherein a reference set may include three-dimensional data points collected from the body part mirroring an identified target body part (e.g., if the right leg is causing the user pain, then reference set data points are collected from the left leg). In patient evaluation system 400, the user 405 follows the instructions of a virtual guide 410 on a display 415. The virtual guide 410 may include a video or animation, such as of a clinician, or may be generated based on a prescribed range of motion for a movement. In an example, the virtual guide 410 may include a representation of a first limb (e.g., a right leg, for example when the patient has limited movement in the right leg) performing a movement, while the user 405 is instructed to use a second limb (e.g., a "good" left leg). The camera 425 may capture the movement of the user 405 using the "good" second limb. The captured movement may be replayed on the display 415, for example in FIG. 4B, while the user 405 attempts the movement with the "bad" first limb while watching the mirrored "good" first limb on the display 415.

The user 405 may be instructed to perform movements with the body part mirroring the identified target body part (e.g., a healthy target body part). In an example, the user 405 is instructed to perform movements with the left leg 420. The movements of the mirroring target body part, here the left leg 420, may be captured with a camera 425. The camera 425 or other capture device, such as an AR device, may collect the three-dimensional data points from the mirroring target body part as members of the reference set.

Figure 4B:
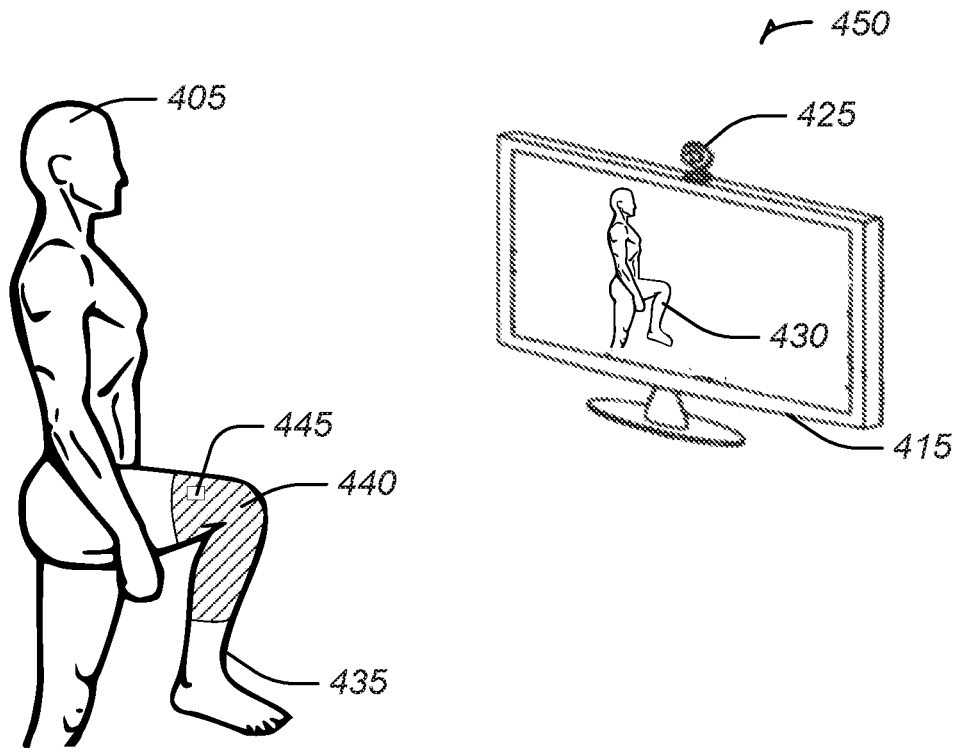

FIG. 4B illustrates a patient evaluation system 450 in accordance with some embodiments. The three-dimensional data points for the measurement set may be collected by capturing the movement the user 405 performs with the identified target body part. In an example, the user 405 is instructed to perform movements with the right leg 435. The display 415 may show the captured video of the movements the user performed with the mirroring target body part as a virtual representation 430 of the user 405. In an example, the user 405 may follow the movements performed with left leg 420 as the virtual representation 430 of the user 405 as the user 405 attempts to match the movements with right leg 435. The movements are captured with camera 425. The camera 425 or other capture device, such as an AR device, may collect the three-dimensional data points from the mirroring target body part as members of the measurement set.

A user 405 may wear an apparatus such as a sleeve 440 on the target body part. The sleeve 440 may include a sensor 445. The sensor 445 may be used to track patient progress, such as a duration or number of repetitions completed by the user 405. In an example, the sensor 445 may be embedded in a user worn apparatus, such as the sleeve 440. This tracked movement may be used to augment movement captured by the camera 425 or a user-facing movement capture apparatus (e.g., a sensor, a sensor array, a camera, an infrared camera, two or more cameras, a depth camera, etc.). Movement of the user 405 may be tracked using a user-facing movement capture apparatus, the camera 425, the sensor, or any of the movement capture apparatus, or the like.

The sensor 445, which may be located in or on sleeve 440 may include an accelerometer, a magnetometer, a gyroscope, an optical sensor, an ultrasonic sensor, an inertial measurement unit, a nine-axis sensor, a contact pressure sensor, or the like. The sensor 445 may include a physiological sensor such as a heart rate monitor, a blood-oxygen monitor, a blood pressure monitor, or the like. The sensor 445 may be used to track movement, guide a movement, count repetitions, measure fatigue, detect muscle fatigue, detect exhaustion, or the like. In an example, a user may be tasked with performing twenty repetitions of a leg lift. Utilizing the sensor 445, such as an accelerometer, a gyroscope, or a nine-axis sensor, the movement of the leg lift may be tracked. The sensor 445 may count the number of leg lift repetitions performed by the user or monitor the form of a leg lift. The sensor 445 may be used to determine if the user is experiencing fatigue or having difficulty completing a repetition or a task. For example, data from the sensor 445 may indicate that a adherence to form is decreasing for subsequently performed leg lifts. Tasks or aspects of a task (e.g., intensity or duration) may be altered in response to determining that the data indicates the proper form is decreasing. In an example, the data may be analyzed to determine the user's level of fatigue from performing repetitions.

The systems and techniques described herein may determine an assessment for a target body part. The assessment may include a physical therapy program to help strengthen the target body part. The worn apparatus sensor 445 may produce data (e.g., whether the user is successfully performing movements, a percentage of successful performance, metrics related to number of repetitions, weight used, etc., or the like) to be used, for example, by a clinician or other caregiver (e.g., a surgeon). The data may be produced after the user performs a movement, completes a scheduled session, or performs at least part of scheduled therapy. The data may be used to adjust prescribed therapy, movement, exercises, medication, surgery timetable, or the like. The user and the clinician may use an AR device or multiple AR devices to share an augmented experience. For example, the clinician may have an AR device, and the AR device of the clinician may display augmented and virtual aspects in a shared environment with an AR device used by the user, overlaid on the same real environment. The clinician may manipulate virtual or real aspects of the shared environment such that the user may see the manipulation.

The display 415 may be used to animate the virtual representation 430 of the user 405 to perform a movement along a path. The path may be used to show a patient how to perform a prescribed movement. The path may be used to determine whether the movement by the user was successful. In an example, the path may be used to determine whether a user has successfully completed an exercise or movement. For example, if the user completes the exercise within the path, the exercise may be determined to be completed successfully. If the user moves outside the path while attempting to complete the exercise, the exercise may be determined to not be completed successfully.

Figure 5:
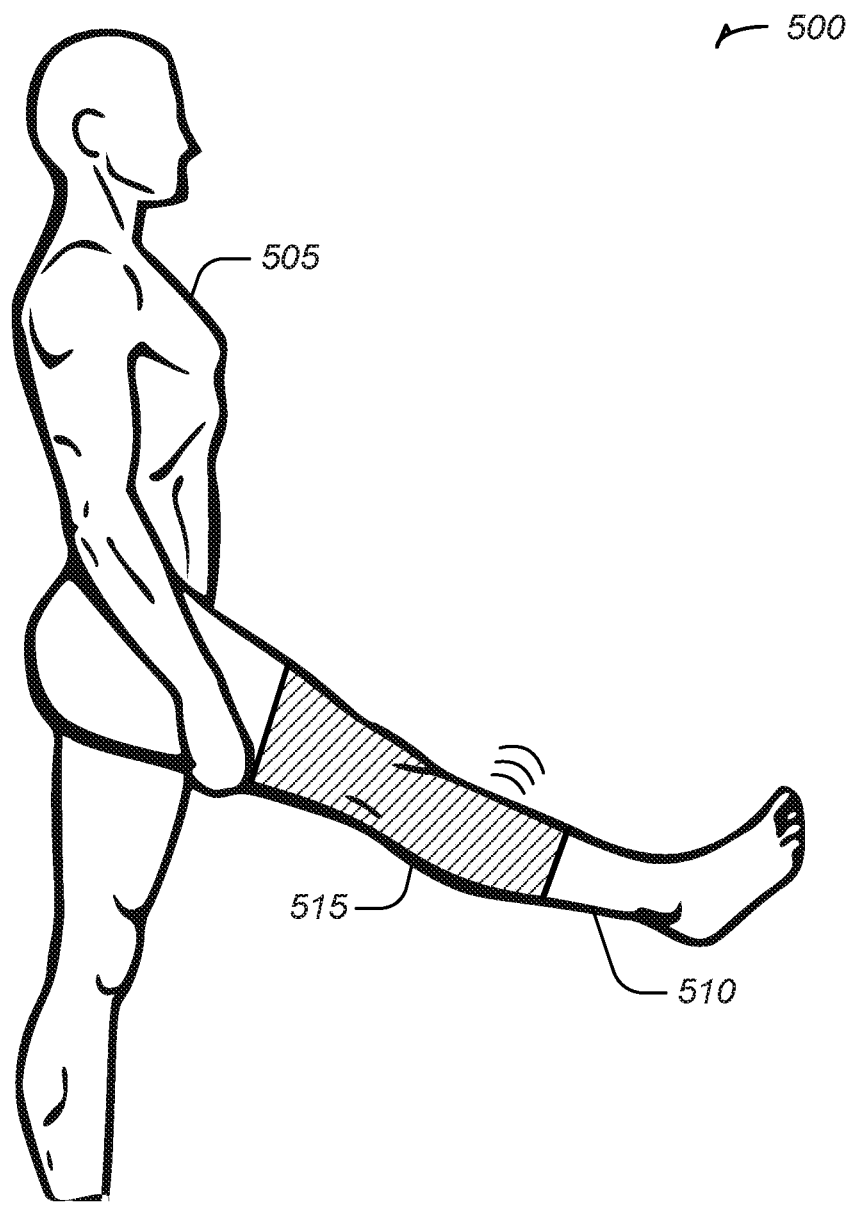
FIG. 5 illustrates an example of a haptic feedback system in accordance with some embodiments.

FIG. 5 illustrates an example of a haptic feedback system 500 in accordance with some embodiments. A worn device 515 or other apparatus including one or more sensors may be worn or attached to a portion of a user 505, such as a target body part 510. The worn device 515 or apparatus may include a mechanism to provide the user 505 with haptic feedback. The worn device 515 or apparatus may be a sleeve, glove, wrist band, ankle band, or include a skin adhesive. In an example, the worn device 515 may be a smartwatch such as the Apple® Watch from Apple of Cupertino, Calif. Utilizing a sensor, such as an accelerometer, the worn device 515 may provide haptic feedback to the user 505 to indicate the target body part 510 has reached a predetermined position. When the user 505 receives a physical therapy program, the haptic feedback may be used to guide the user 505 through the program. The haptic feedback may alert the user 505 when the target body part 510 has reached the predetermined position or has completed a prescribed number of repetitions.

The worn device 515 or an apparatus may include one or more haptic components to guide the movement of a target body part through a specific movement. For example, a user may wear a sleeve apparatus on a leg with a first haptic component located on an inner leg portion of the sleeve and a second haptic component located on an outer leg portion of the sleeve. As the user performs the specific movement, when the leg begins the stray either outward or inward, then the respective haptic component may provide feedback to alert the user to straighten the leg. For example, if the leg moves inward, the first haptic component on the inner leg portion of the sleeve may vibrate to alert the user that the leg is moving inward, and allow the user to correct the movement. In another example, the haptic components may be used to guide the user through a movement by vibrating in a direction that the user is to move. For example, the sleeve may include haptic components on a front and a back portion of the sleeve, the front haptic component vibrating to indicate the user is to move the leg in an extension movement, and the back haptic component vibrating to indicate the user is to move the leg in a flexing movement. In yet another example, a haptic component may be used to indicate completion of a movement (e.g., for a movement from flexion to extension, the haptic component may vibrate when the angle of the leg reaches a threshold, such as close to extension).

Figure 6:
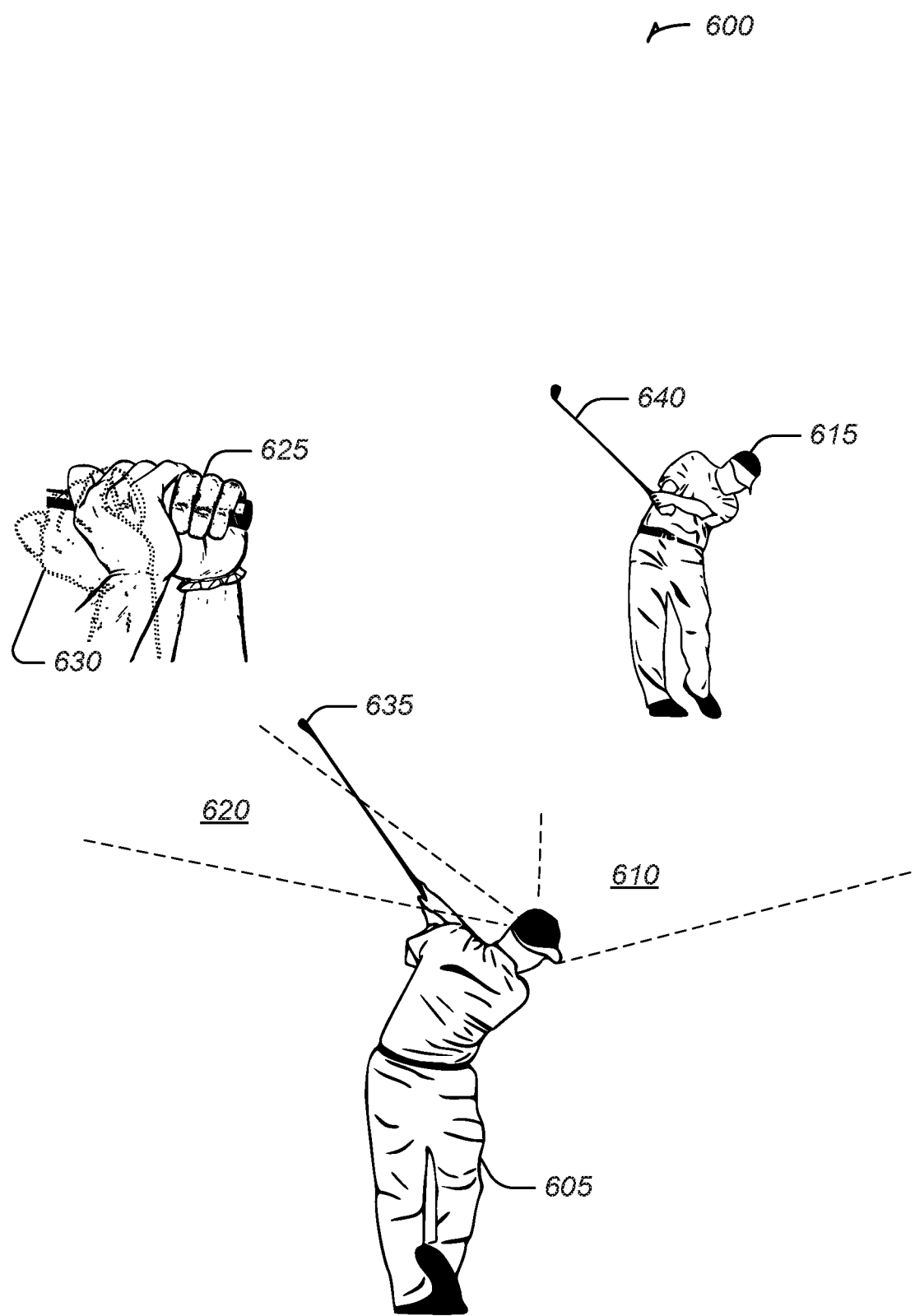
FIG. 6. illustrates real and virtual aspects of a sports training augmented reality system in accordance with some embodiments.

FIG. 6. illustrates real and virtual aspects of a sports training AR system 600 in accordance with some embodiments. The sports training AR system 600 may be used for strengthening or improving physical movement, such as for a sporting performance. For example, a user may wish to increase extension of a golf swing or gain a greater range of motion when throwing a baseball or football. The sports training AR system 600 may capture the movements of a user 605 with a camera or any of the other previously described devices such as an AR device or motion sensitive sensor. In an example, the user may wear an AR device, such as AR glasses, to augment what is viewed by the user 605 or a virtual reality (VR) device, such as VR glasses, to view virtual reality aspects. The user may see, by way of the AR glasses, an avatar 615 within an AR or VR field of view in a first direction 610. The avatar 615 may be used to demonstrate the proper motions for a user 605. In an example, when the user 605 wishes to improve a golf swing, the avatar 615 may perform the swing such the user 605 may watch and mimic the performance by the avatar 615.

In an example, the user 605 may control movement of the avatar 615. For example, the user 605 may hold an apparatus used for a sport such as a golf club or baseball bat. The sport apparatus may have a motion sensitive sensor such as an accelerometer, a gyroscope, an inertial measurement unit, or a nine-axis sensor. The motion sensor may track the movement of the sport apparatus. The tracked movement may be used by the sports training AR system 600 to display the movement using a representation of the movement via the avatar 615 performing the movement virtually. In another example, the avatar 615 may be used to display a training movement. For example, the training movement may represent an idealized or professional movement of the sport movement attempted by the user 605. The user 605 may control the avatar 615 using the sport apparatus 635 such that the avatar 615 moves a corresponding virtual sport apparatus 640 similarly to the sport apparatus 635. The avatar 615 may move the virtual sport apparatus 640 according to the training movement. Thus the movement of the avatar 615 may generally follow the movement of the user 605, but may differ by displaying an improved or training movement for the user to attempt to match. In this way, the user 605 may move and control the sport apparatus 635 while viewing similar movements by the virtual sport apparatus 640, the similar movements representing an ideal or improved movement.

The movements of the user 605 may be captured through a camera or sensor attached to the user 605 or to a sports instrument, such as a golf club or baseball bat. The user 605 may be instructed, such as using an avatar 615 on a display or within an AR field of view in the first direction 610, to perform a movement related to the predetermined sports movement. In an example, three-dimensional data points of the user's movements are captured as a measurement set. The three-dimensional data points of the measurement set may be classified to produce a movement set which includes the range of motion for the target body parts related to the sports movement. A reference set corresponding to the sports movement may be obtained. In an example, the reference set may include three-dimensional data points captured from multiple professional athletes of the corresponding sport. A different set may be computed wherein a member of the difference set defines a three-dimensional relationship between a member of the movement set and a corresponding member of the reference set. An assessment for how the user 605 may improve performance may be determined based on the difference set. The assessment may include a physical therapy program, a stretch the user performs before the sports activity, or a movement or strengthening technique the user 605 is guided through by the avatar 615.

As the user 605 turns and moves, the type of assistance provided through an AR device may change. In an example, the user 605 may view the avatar 615 when looking in a first direction 610 or at a first depth, and when the user 605 is looking in a second direction 620 or at a second depth and views an arm or a leg of the user, other virtual guidance information may be displayed. The other virtual guidance information may include an arrow pointing to a correct positioning, an overlay of a virtual arm or a virtual leg, a virtual movement indicator (e.g., a symbol indicating rotation to be applied), an alert, audible feedback, haptic feedback, or the like. In an example, the user 605, while performing a golf swing, may change views from the first direction 610 or first depth to the second direction 620 or the second depth, such as to view hand positioning at the completion of a swing. The user 605, through the AR glasses, may view an augmented view of the user's hands and end of a club. The user may view the hands 625 as they grip the golf club The augmented view may display to the user 605 a virtual representation 630 of a hand position. The virtual representation 630 may include a virtual hand or hands positioned according to a predetermined improvement or change to the user's 605 hand position. For example, the virtual representation 630 may represent a change to a grip or hand position at the end of a swing to improve the swing. The user 605, while using an AR device, may select a type of augmentation to improve performance. The type of augmentation may include an instructor, an overlaid virtual representation of a limb positioning, a virtual arrow or other virtual icon to demonstrate a predetermined path of motion or configuration, or a virtually represented recreation of a previous movement by the user 605.

Figure 7:
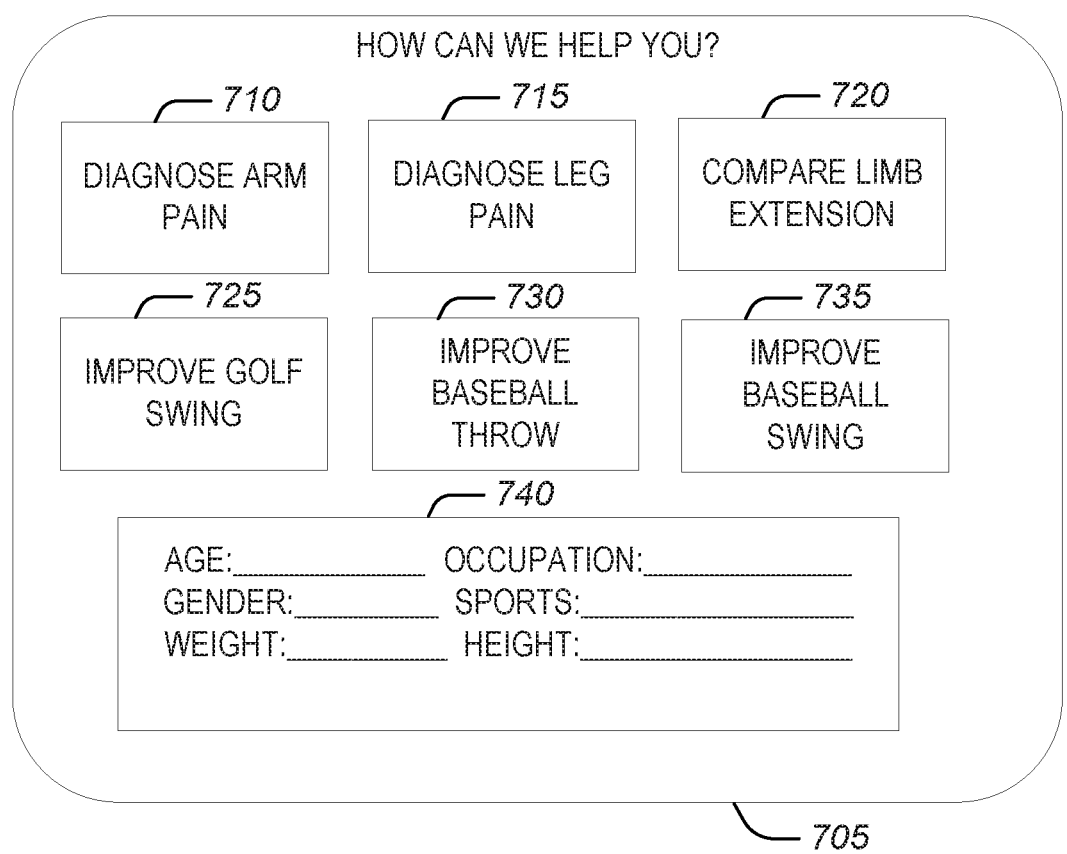
FIG. 7 illustrates a user interface in accordance with some embodiments.

FIG. 7 illustrates a user interface 705 in accordance with some embodiments. The user interface 705 may be used to allow a user to select from among types of assessments. The user interface 705 may prompt the user to select a program assessment concerning a pain or issue with a target body part (e.g., diagnosing arm pain 710 or diagnosing leg pain 715). The user interface 705 may prompt the user to select a program to determine movement and range of motion differences between mirroring limbs (e.g., comparing limb extension 720. The user interface 705 may prompt the user to select a program to assist the user with a sports performance (e.g., improving a golf swing 725, improving a baseball throw 730, or improving a baseball swing 735). Upon selection of a program, the system may begin the diagnosis for the selected program. The diagnosis may include any of the previous described programs such as tasking the user to perform a set of movements with the identified target body part or perform the identified sports movement.

The user interface 705 may prompt the user for additional information, such as demographic information, pain information, etc. The user information prompt 740 may query the user for data about the user such as the user's age, occupation, gender, weight, height, and sports the user participates in. The information input by the user may be used to select a set of data to be used as the reference set of data, wherein the selected set of data has similar corresponding characteristics. Once selected by the user, the user interface 705 may display aspects of a physical therapy program, movements, etc. (e.g., as described above). In an example, the user interface 705 may be presented on a display screen. In another example, the user interface 705 may be displayed using an AR device.

Figure 8:
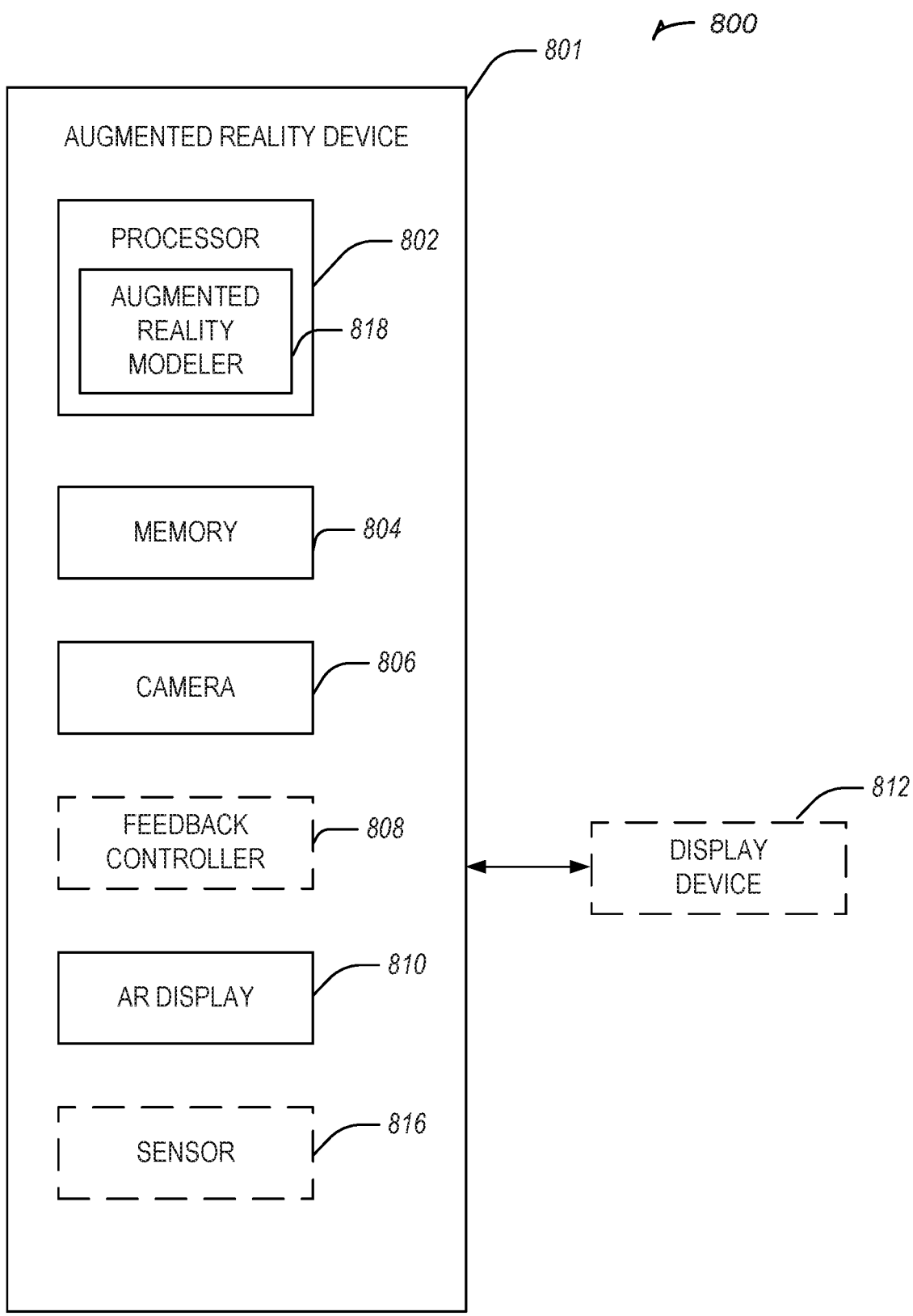
FIG. 8 illustrates an augmented reality diagnosis system including an augmented reality device in accordance with some embodiments.

FIG. 8 illustrates an augmented reality diagnosis system 800 in accordance with some embodiments. The augmented reality diagnosis system 800 includes an augmented reality device 801, and may include a display device 812. The augmented reality device 801 includes a processor 802, memory 804, a camera 806, and an AR display 810. The augmented reality device 801 may include a feedback controller 808 or a sensor 816. The augmented reality device may be connected to the display device 812, which may display video or other aspects. In an example, the augmented reality device 801 may be a HoloLens manufactured by Microsoft of Redmond, Wash. The processor 802 of the augmented reality device 801 includes an augmented reality modeler 818. The augmented reality modeler 818 may be used by the processor 802 to create the augmented reality environment. For example, the augmented reality modeler 818 may receive dimensions of a room, such as from the camera 806 or sensor 816, and create the augmented reality environment to fit within the physical structure of the room. In another example, physical objects may be present in the room and the augmented reality modeler 818 may use the physical objects to present virtual objects in the augmented reality environment. For example, the augmented reality modeler 818 may use or detect a table present in the room and present a virtual object as resting on the table. In an example, a plurality of physical items may be used by a user to interact with the virtual target. The virtual object may be used by a user to complete a physical therapy movement.

The processor 802 may identify an object in a real environment, such as through processing information received using the camera 806. For example, the processor 802 may receive information, such as an image or a series of images from the camera 806 and identify in the image or the series of images, the object. The processor 802 may create virtual target (e.g., a line, a circle, etc.) in an augmented reality (AR) environment. The virtual target may have a fixed position, such as a position fixed with respect to the object. For example, the virtual target may be positioned in the AR environment such that the virtual target remains fixed when the AR device 801 moves. In an example, the virtual target may be fixed without respect to a view presented to a user of the AR device.

The AR display 810 may display the AR environment overlaid on the real environment. The display AR 810 may show the virtual target, using the AR device 801, in the fixed position in the AR environment. In an example, the AR device 801 may remove the virtual target from display in the AR environment in response to detecting a user interaction with the virtual target. For example, when the virtual target is a line or circle, the virtual target may be removed (e.g., fade out, popped, explode, etc.) when a user interacts with the virtual target (e.g., kicks the circle, moves a body part past the line, etc.).

In an example, the camera 806 may be used to identify the object in the real environment. The camera 806 may send information, such as images to the processor 802 about the object, and the processor 802 may use the raw information (e.g., raw images) to identify the object in the real environment. The augmented reality device 801 may include a sensor 816, such as an infrared sensor. In another example, the sensor may be on the object. In an example, the processor 802 may receive information from the sensor 816 on the object to identify the object. The camera 806 or the sensor 816 may be used to detect movement that may be interpreted by the processor 802 as attempted or intended interaction by the user with the virtual target.

In an example, the camera 806 or other motion capture device such as an infrared capture device, may capture a series of images of three-dimensional movement of a target body part of a subject, the target body part moving relative to a reference point of the subject. The processor 802 may determine range of motion information for the target body part based on the captured series of images. In an example, the processor 802 may obtain a reference range of motion capabilities for the target body part. The processor 802 may determine that the reference range of motion capabilities exceed the range of motion for the target body part. In an example, the display device 812 or the AR display 810 may display, in response to the determination, a virtual animation of the target body part, the virtual animation created using the reference range of motion capabilities and the range of motion information for the target body part. The virtual animation may be displayed using the AR display 810 as a virtual aspect represented in a real environment, such as in a room or augmented over the target body part of the subject.

Figure 9:
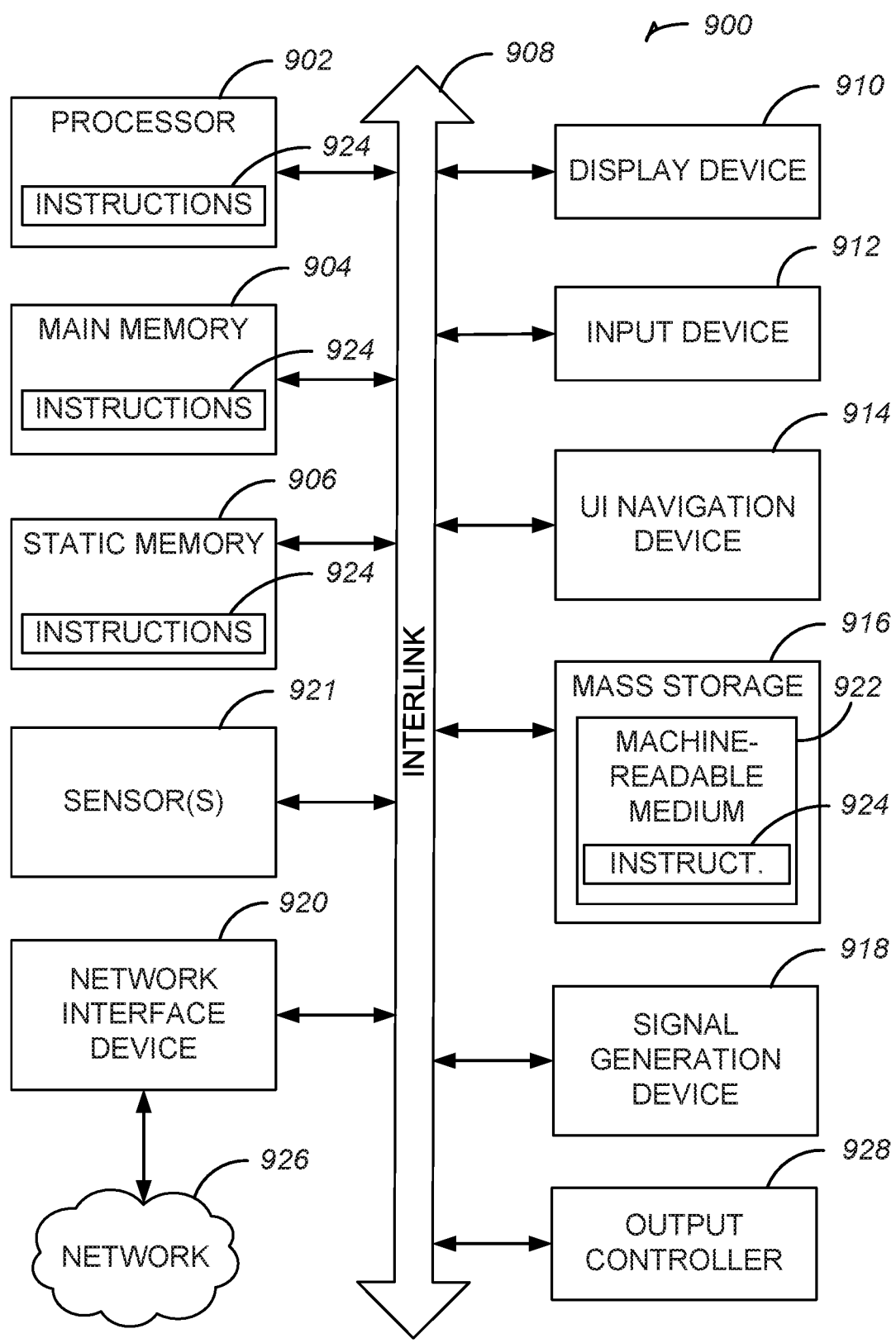
FIG. 9 illustrates generally an example of a block diagram of a machine upon which any one or more of the techniques discussed herein may perform in accordance with some embodiments.

FIG. 9 illustrates a block diagram of an example machine 900 upon which any one or more of the techniques (e.g., methodologies) discussed herein may perform. In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910, an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine readable medium 922 is illustrated as a single medium, the term "machine readable medium" may include a single medium or multiple media (e.g., a centralized or distributed database, and/or associated caches and servers) configured to store the one or more instructions 924. The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 924 may further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Figure 10:
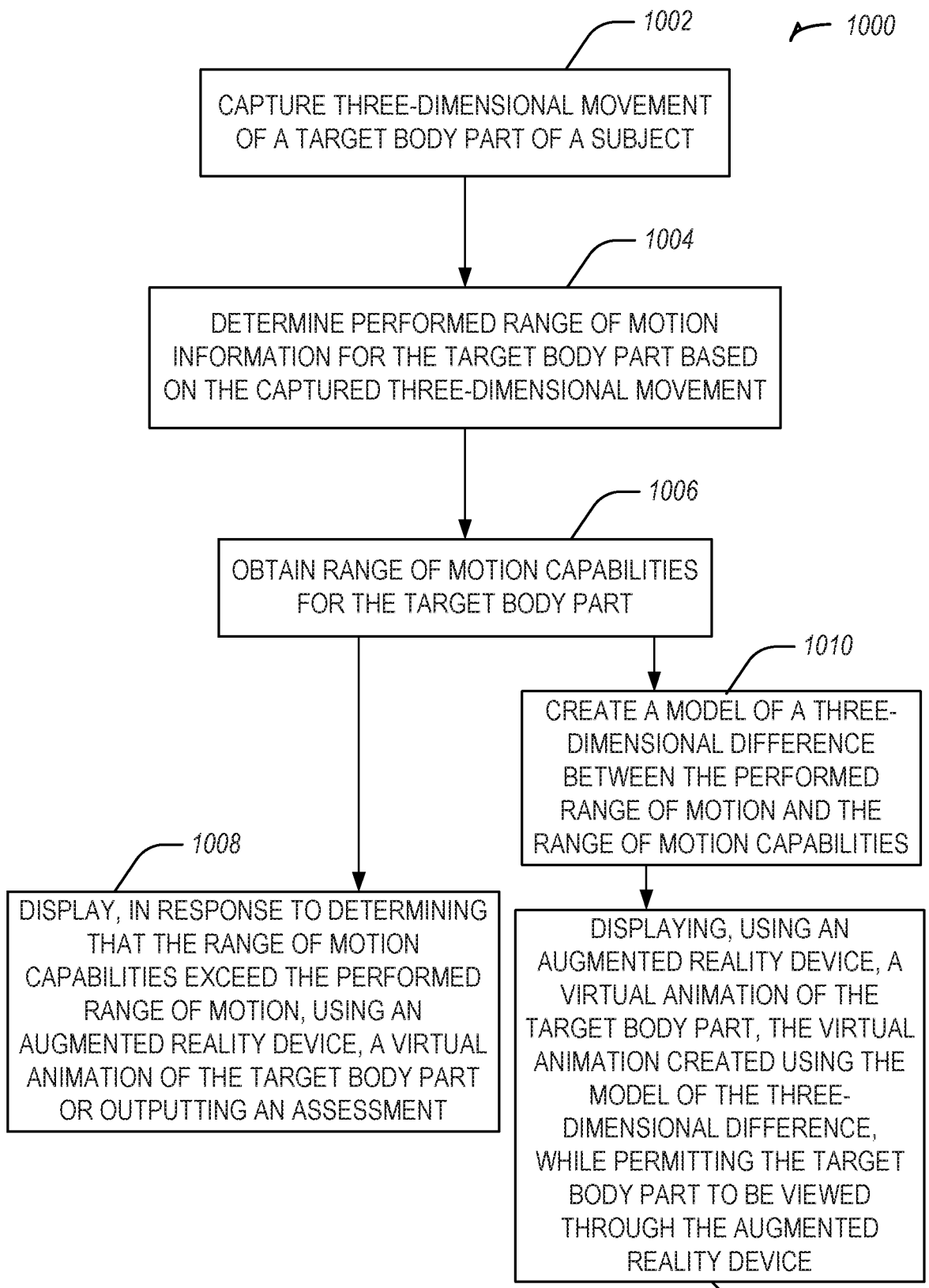
FIG. 10 illustrates a flow chart showing a technique for displaying an virtual animation of a target body part or outputting an assessment in accordance with some embodiments.

FIG. 10 illustrates a flow chart showing a technique 1000 for displaying an virtual animation of a target body part or outputting an assessment. The technique 1000 includes an operation 1002 to capture three-dimensional movement of a target body part of a subject. The technique 1000 includes an operation 1004 to determine performed range of motion information for the target body part based on the captured three-dimensional movement. The technique 1000 includes an operation 1006 to obtain range of motion capabilities for the target body part. The technique 1000 may include an operation 1008 to display, in response to determining that the range of motion capabilities exceed the performed range of motion, using an augmented reality device, a virtual animation of the target body part or outputting an assessment. The technique 1000 may include further operations or elements, such as those described below in the various examples. Each of these non-limiting examples may stand on its own, or may be combined in various permutations or combinations with one or more of the other examples.

The technique 1000 may include an operation to create a model of a three-dimensional difference between the performed range of motion and the range of motion capabilities. The technique 1000 may include an operation to displaying, using an augmented reality device, a virtual animation of the target body part, the virtual animation created using the model of the three-dimensional difference, while permitting the target body part to be viewed through the augmented reality device. In an example, operation 1008 may be performed in conjunction with operations 1010 and 1012 or 1008 may be substituted for or by operations 1010 and 1012.

Figure 11:
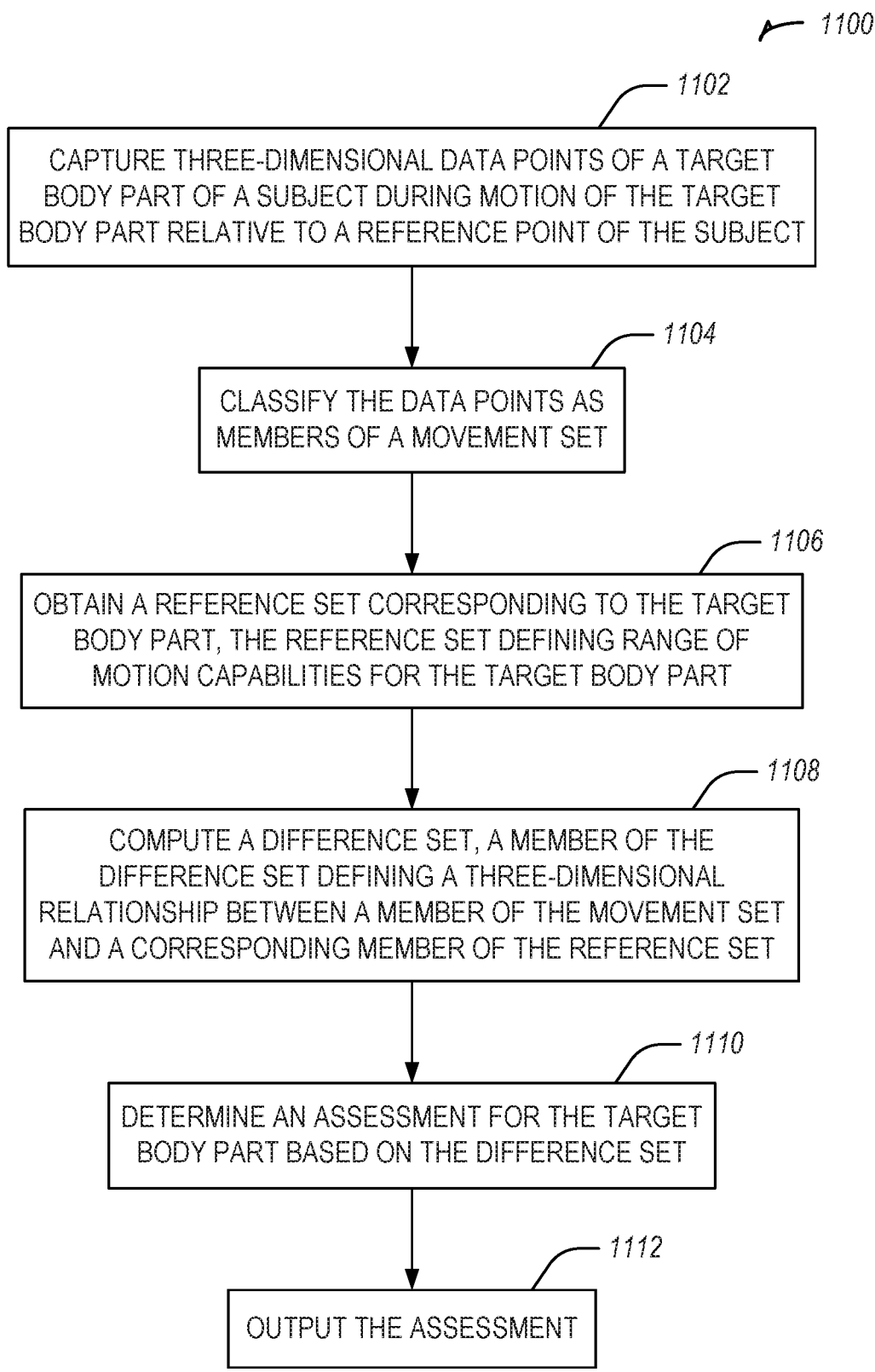
FIG. 11 illustrates a flow chart showing a technique 1100 for assessing range of motion of a target body part in accordance with some embodiments.

FIG. 11 illustrates a flow chart showing a technique 1100 for assessing range of motion of a target body part according to an example. The technique 1100 includes an operation 1102 to capture three-dimensional data points of a target body part of a subject during motion of the target body part relative to a reference point of the subject. Operation 1102 may include capturing sequential images, such as using a visible light camera, a depth camera, an infrared camera, or other motion capture apparatus. In an example, operation 1102 may include capturing information at a series of points (e.g., positions of the target body part or points based on time intervals, such as once a millisecond) using a sensor affixed to the target body part or affixed to the subject such that movement of the target body part may be tracked. The sensor may include an accelerometer, an inertial measurement unit (IMU), a contact pressure sensor, or the like. The sensor may be embedded in a wearable device (e.g., a smartwatch).

The technique 1100 includes an operation 1104 to classify the data points as members of a movement set. The data points may range of motion information for the target body part, such as during the motion. In an example, the movement set may include a maximum angle of extension of the target body part and the reference set may include a maximum angle of extension for a reference body part matching or mirroring the target body part. The difference set includes a difference of maximum angle of extension between the movement set and the reference set The technique 1100 includes an operation 1106 to obtain a reference set corresponding to the target body part, the reference set defining range of motion capabilities for the target body part. In an example, the reference set may be determined based on a second set of three-dimensional data points collected from a reference body part of the subject that mirrors the target body part, the reference body part having a greater range of motion than the target body part.

The technique 1100 includes an operation 1108 to compute a difference set, a member of the difference set defining a three-dimensional relationship between a member of the movement set and a corresponding member of the reference set. In an example, the difference set may include an angle of difference between the rage of motion data of the reference set and the range of motion data of the movement set. In an example, the difference set includes a difference of maximum angle of extension between the movement set and the reference set The technique 1100 includes an operation 1110 to determine an assessment for the target body part based on the difference set. In an example, the assessment may be a physical therapy program, such as including a movement challenge or procedure for the target body part. The assessment may indicate whether the target body part requires surgery.

The technique 1100 includes an operation 1112 to output the assessment. Operation 1112 may include outputting the assessment to an augmented reality display for display on the augmented reality display. In an example, operation 1112 includes generating a virtual component for display using the reference set. This example may include displaying the virtual component using an augmented reality display, while permitting the target body part to be viewed through the augmented reality display. The subject may be guided to perform movement with the target body part mimicking the virtual component, such as with an indication displayed on the augmented reality display or via haptic feedback (e.g., with a plurality of haptic feedback devices which may be affixed to parts of the subject, such as the target body part).

The technique 1100 may include determining performed range of motion information for the target body part based on the movement set. The technique 1100 may include obtaining range of motion capabilities for the target body part. In an example, obtaining the range of motion capabilities includes obtaining the range of motion capabilities from a database. The technique 1100 may include training range of motion capabilities data using a machine-learning technique. The range of motion capabilities to be retrieved from the database may be queried from the database from the learned range of motion capabilities (e.g., output from the machine learning system). In another example, obtaining the range of motion capabilities includes obtaining the range of motion capabilities from the camera by capturing a reference body part of the subject that mirrors the target body part, the reference body part performing the three-dimensional movement.

The technique 1100 may include creating a model of a three-dimensional difference between the performed range of motion and the range of motion capabilities. In an example, using an augmented reality device, a virtual animation of the target body part may be displayed. The virtual animation may be created using the model of the three-dimensional difference, while permitting the target body part to be viewed through the augmented reality device Example 1 is a method comprising: capturing three-dimensional data points of a target body part of a subject during a series of motions, the target body part being mobile relative to a reference point of the subject, wherein the data points are members of a measurement set; classifying members of the measurement set to produce a movement set, members of the movement set including range of motion information for the target body part; obtaining a reference set corresponding to the target body part, the reference set defining range of motion capabilities for the target body part; computing a difference set, a member of the difference set defining a three-dimensional relationship between a member of the movement set and a corresponding member of the reference set; determining an assessment for the target body part based on the difference set; and outputting the assessment.

In Example 2, the subject matter of Example 1 optionally includes wherein the assessment indicates the target body part requires surgery.

In Example 3, the subject matter of any one or more of Examples 1-2 optionally include wherein the assessment includes a list of activities the subject should refrain from performing.

In Example 4, the subject matter of any one or more of Examples 1-3 optionally include wherein the assessment is output to a display screen.

In Example 5, the subject matter of any one or more of Examples 1-4 optionally include wherein the assessment is output to an augmented reality display.

In Example 6, the subject matter of any one or more of Examples 1-5 optionally include wherein the assessment is output to a clinician display.

In Example 7, the subject matter of any one or more of Examples 1-6 optionally include wherein the measurement set includes sequential images of the target body part.

In Example 8, the subject matter of Example 7 optionally includes wherein the sequential images are captured with a camera.

In Example 9, the subject matter of any one or more of Examples 7-8 optionally include wherein the sequential images are captured with a depth detection camera.

In Example 10, the subject matter of any one or more of Examples 1-9 optionally include wherein the three-dimensional data points are captured with a movement capture apparatus.

In Example 11, the subject matter of any one or more of Examples 1-10 optionally include wherein the difference set includes an angle of difference between the range of motion data of the reference set and the range of motion data of the movement set.

In Example 12, the subject matter of any one or more of Examples 1-11 optionally include wherein the measurement set includes values recorded from sensors detecting movement from the target body part.

In Example 13, the subject matter of Example 12 optionally includes wherein the sensors include accelerometers.

In Example 14, the subject matter of any one or more of Examples 12-13 optionally include wherein the sensors include an inertial measurement unit (IMU).

In Example 15, the subject matter of any one or more of Examples 12-14 optionally include wherein the sensors include a nine-axis sensor.

In Example 16, the subject matter of any one or more of Examples 12-15 optionally include wherein the sensors include contact pressure sensors.

In Example 17, the subject matter of any one or more of Examples 12-16 optionally include wherein the target body part is a leg, wherein to measure the movement of the leg a first sensor is placed above the knee of the leg and second sensor is placed below the knee of the leg.

In Example 18, the subject matter of any one or more of Examples 12-17 optionally include wherein at least one of the sensors are embedded in a wearable sleeve.

In Example 19, the subject matter of any one or more of Examples 1-18 optionally include wherein the series of motions include a set of resistance tests.

In Example 20, the subject matter of any one or more of Examples 1-19 optionally include wherein the series of motions include a set of guided movement tests.

In Example 21, the subject matter of any one or more of Examples 1-20 optionally include wherein an artificial neural network is used to determine the movement set.

In Example 22, the subject matter of any one or more of Examples 1-21 optionally include wherein the movement set range of motion information includes the maximum angle of extension of the target body part.

In Example 23, the subject matter of any one or more of Examples 1-22 optionally include wherein the movement set includes the maximum angle of extension of the target body part and the reference set includes the maximum angle of extension for a body part matching the target body part, wherein the difference set includes the difference of maximum angle of extension between the movement set and the reference set.

In Example 24, the subject matter of Example 23 optionally includes wherein the assessment includes movement challenges to decrease the range of motion difference between the movement set and the reference set.

In Example 25, the subject matter of any one or more of Examples 23-24 optionally include wherein the assessment includes movement challenges to increase the maximum range of motion of the target body part.

In Example 26, the subject matter of any one or more of Examples 1-25 optionally include wherein the movement set defines the range of motion for a joint of the target body part.

In Example 27, the subject matter of Example 26 optionally includes wherein the joint is the knee.

In Example 28, the subject matter of any one or more of Examples 26-27 optionally include wherein the joint is the elbow.

In Example 29, the subject matter of any one or more of Examples 1-28 optionally include wherein the reference set includes movement data corresponding to a matching body part of the subject.

In Example 30, the subject matter of any one or more of Examples 1-29 optionally include wherein the reference set includes collected movement data normative to the age of the subject.

In Example 31, the subject matter of any one or more of Examples 1-30 optionally include wherein the reference set includes collected movement data normative to the occupation of the subject.

In Example 32, the subject matter of any one or more of Examples 1-31 optionally include wherein the reference set includes collected movement data normative to the gender of the subject.

In Example 33, the subject matter of any one or more of Examples 1-32 optionally include wherein the reference set includes collected movement data normative to the height, weight, or combination of height and weight of the subject.

In Example 34, the subject matter of any one or more of Examples 1-33 optionally include wherein the reference set includes collected movement data normative to the physical activities of the subject.

In Example 35, the subject matter of any one or more of Examples 1-34 optionally include wherein the reference set includes collected movement data normative to the degree of pain the experienced by the subject.

In Example 36, the subject matter of any one or more of Examples 1-35 optionally include wherein the subject may select a reference set, wherein the selectable reference set includes range of motion capabilities for a target body part to perform a movement of a sport.

In Example 37, the subject matter of any one or more of Examples 1-36 optionally include wherein the assessment comprises a series of movement challenges for the target body part.

In Example 38, the subject matter of Example 37 optionally includes wherein the assessment is a physical therapy program.

In Example 39, the subject matter of any one or more of Examples 37-38 optionally include wherein the movement challenges for the target body part are administered through an augmented reality device.

In Example 40, the subject matter of Example 39 optionally includes displaying a virtual component using an augmented reality display, associated with the augmented reality device, while permitting the target body part to be viewed through the augmented reality display; guiding the subject, with images displayed on the augmented reality display, to perform movements with the target body part.

In Example 41, the subject matter of any one or more of Examples 1-40 optionally include displaying a virtual component using an augmented reality display while permitting the target body part to be viewed through the augmented reality display; guiding the subject, with images displayed on the augmented reality display, to perform movements with the target body part; capturing the movements of the target body part with the augmented reality device to collect data points as members of the measurement set.

In Example 42, the subject matter of any one or more of Examples 1-41 optionally include displaying a virtual component using an augmented reality display, associated with the augmented reality device, while permitting the target body part to be viewed through the augmented reality display; guiding the subject, with images displayed on the augmented reality display, to perform movements with the target body part; obtaining the range of motion for the target body part with the augmented reality system.

In Example 43, the subject matter of any one or more of Examples 1-42 optionally include displaying a virtual component using an augmented reality display, associated with the augmented reality device, while permitting a body part matching the target body part to be viewed through the augmented reality display; guiding the subject, with images displayed on the augmented reality display, to perform movements with the body part matching the target body part; and capturing the movements of the body part matching the target body part with the augmented reality device to collect data points as members of the reference set.

In Example 44, the subject matter of any one or more of Examples 1-43 optionally include displaying a virtual component using an augmented reality display, associated with the augmented reality device, while permitting a body part matching the target body part to be viewed through the augmented reality display; guiding the subject, with images displayed on the augmented reality display, to perform movements with the body part matching the target body part; and capturing, with the augmented reality device, the movements of the body part matching the target body part.

In Example 45, the subject matter of Example 44 optionally includes displaying a virtual component using an augmented reality display, associated with the augmented reality device, while permitting the target body part to be viewed through the augmented reality display; guiding the subject, with guide images displayed on the augmented reality display, to perform movements with the target body part, wherein the guide images are based on the captured movements of the body part matching the target body part; and capturing the movements of the target body part with the augmented reality device to collect data points as members of the measurement set.

In Example 46, the subject matter of any one or more of Examples 37-45 optionally include guiding the movement of the subject through the movement challenges with haptic feedback.

In Example 47, the subject matter of Example 46 optionally includes wherein guiding the movement of the subject includes providing haptic feedback directly to the target body part with a plurality of haptic feedback devices.

In Example 48, the subject matter of any one or more of Examples 46-47 optionally include wherein the haptic feedback is provided to the target body part by a wearable device.

In Example 49, the subject matter of any one or more of Examples 1-48 optionally include monitoring the movement challenges using artificial intelligence, wherein the assessment is determined by the artificial intelligence system.

In Example 50, the subject matter of any one or more of Examples 37-49 optionally include wherein the movement challenges are monitored by a clinician and wherein the assessment is output to a display for the clinician.

In Example 51, the subject matter of any one or more of Examples 1-50 optionally include wherein the assessment is determined by an artificial intelligence system.

In Example 52, the subject matter of any one or more of Examples 1-51 optionally include wherein the assessment is determined by a clinician.

In Example 53, the subject matter of any one or more of Examples 1-52 optionally include wherein a member of the difference set is a magnitude of difference.

In Example 54, the subject matter of any one or more of Examples 1-53 optionally include wherein a member of the difference set is a directional distance.

In Example 55, the subject matter of any one or more of Examples 1-54 optionally include wherein to member of the difference set is a mapping from the movement set to the reference set.

Example 56 is a method comprising: capturing three-dimensional data points of a target body part of a subject during a series of motions, the target body part being target relative to a reference point of the subject, wherein the data points are members of a measurement set; determining performed range of motion information for the target body part based on the measurement set; obtaining a reference set corresponding to the target body part, the reference set defining range of motion capabilities for the target body part; computing a difference set based on the measurement set and the reference set, a member of the difference set defining a three-dimensional relationship between a member of the measurement set and a corresponding member of the reference set; determining an assessment for the target body part based on the difference set; and outputting the assessment.

Example 57 is a method comprising: capturing, for example, by a camera of an in-store kiosk, three-dimensional movement of a target body part of a subject, the target body part moving relative to a reference point of the subject; determining performed range of motion information for the target body part based on the captured three-dimensional movement; obtaining range of motion capabilities for the target body part; creating a model of a three-dimensional difference between the performed range of motion and the range of motion capabilities; and displaying, using an augmented reality device, a virtual animation of the target body part, the virtual animation created using the model of the three-dimensional difference.

Example 58 is a method comprising: capturing, for example, by a camera of an in-store kiosk, three-dimensional movement of a target body part of a subject, the target body part moving relative to a reference point of the subject; determining performed range of motion information for the target body part based on the captured three-dimensional movement; obtaining range of motion capabilities for the target body part; determining that the range of motion capabilities exceed the performed range of motion; and displaying, in response to the determination, using an augmented reality device, a virtual animation of the target body part, the virtual animation created using the range of motion capabilities and the performed range of motion.

In Example 59, the subject matter of Example 58 optionally includes wherein obtaining includes obtaining from a database or from the camera, wherein when obtaining from the camera includes capturing the body part matching the target body part.

In Example 60, the subject matter of Example 59 optionally includes training range of motion capabilities data using a machine-learning technique, and wherein obtaining from the database includes querying the database for the range of motion capability from learned range of motion capabilities.

Example 61 is a system for performing any of the methods of Examples 1-60, the system including components for performing the methods, such as a processor, memory, an augmented reality device, a camera, an in-store kiosk, a display screen, a transceiver, a server, a database, or the like.

Example 62 is a machine readable medium including instructions, which when executed, cause a processor or machine to perform any of the methods of Examples 1-60.

Example 63 is a system for diagnosing an issue with a target body part, the system comprising: a motion capture device to capture a series of images of three-dimensional movement of the target body part of a subject, the target body part moving relative to a reference point of the subject; a processor to: determine range of motion information for the target body part based on the captured series of images; obtain a reference range of motion capabilities for the target body part; determine that the reference range of motion capabilities exceed the range of motion for the target body part; and an augmented reality device to: display, in response to the determination, using the augmented reality device, a virtual animation of the target body part, the virtual animation created using the reference range of motion capabilities and the range of motion information for the target body part.

In Example 64, the subject matter of any one or more of Examples 61-63 optionally include wherein the motion capture device is one of a camera, an image capture device, or an infrared camera.

Example 65 is a method for assessing range of motion comprising: capturing three-dimensional data points of a target body part of a subject during motion of the target body part relative to a reference point of the subject; classifying the data points, including range of motion information for the target body part, as members of a movement set; obtaining a reference set corresponding to the target body part, the reference set defining range of motion capabilities for the target body part; computing a difference set, a member of the difference set defining a three-dimensional relationship between a member of the movement set and a corresponding member of the reference set; determining an assessment for the target body part based on the difference set; and outputting the assessment.

In Example 66, the subject matter of Example 65 includes, wherein the assessment indicates that the target body part requires surgery.

In Example 67, the subject matter of Examples 65-66 includes, determining the reference set based on a second set of three-dimensional data points collected from a reference body part of the subject that mirrors the target body part, the reference body part having a greater range of motion than the target body part.

In Example 68, the subject matter of Examples 65-67 includes, wherein outputting the assessment includes outputting the assessment to an augmented reality display for display on the augmented reality display.

In Example 69, the subject matter of Examples 65-68 includes, wherein capturing the data points includes capturing sequential images using a depth camera.

In Example 70, the subject matter of Examples 65-69 includes, wherein the difference set includes an angle of difference between the range of motion data of the reference set and the range of motion data of the movement set.

In Example 71, the subject matter of Examples 65-70 includes, wherein capturing the data points includes capturing information at a series of points using a sensor affixed to the target body part, wherein the sensor includes an accelerometer, an inertial measurement unit (IMU), or a contact pressure sensor, and wherein the sensor is embedded in a wearable sleeve.

In Example 72, the subject matter of Examples 65-71 includes, wherein the movement set includes a maximum angle of extension of the target body part and the reference set includes a maximum angle of extension for a reference body part matching the target body part, and wherein the difference set includes a difference of maximum angle of extension between the movement set and the reference set.

In Example 73, the subject matter of Examples 65-72 includes, wherein the assessment is a physical therapy program including a movement challenge for the target body part.

In Example 74, the subject matter of Examples 65-73 includes, wherein outputting the assessment includes: generating a virtual component for display using the reference set; displaying the virtual component using an augmented reality display, while permitting the target body part to be viewed through the augmented reality display; guiding the subject, with an indication displayed on the augmented reality display, to perform movement with the target body part mimicking the virtual component.

In Example 75, the subject matter of Example 74 includes, wherein guiding the subject includes providing haptic feedback to the target body part with a plurality of haptic feedback devices.

Example 76 is at least one non-transitory machine-readable medium including instructions for assessing range of motion, which when executed by a machine, cause the machine to perform operations comprising: capturing three-dimensional movement of a target body part of a subject, the target body part moving relative to a reference point of the subject; determining performed range of motion information for the target body part based on the captured three-dimensional movement; obtaining range of motion capabilities for the target body part; creating a model of a three-dimensional difference between the performed range of motion and the range of motion capabilities; and displaying, using an augmented reality device, a virtual animation of the target body part, the virtual animation created using the model of the three-dimensional difference, while permitting the target body part to be viewed through the augmented reality device.

In Example 77, the subject matter of Example 76 includes, wherein obtaining the range of motion capabilities includes obtaining the range of motion capabilities from a database.

In Example 78, the subject matter of Example 77 includes, wherein the operations further include training range of motion capabilities data using a machine-learning technique, and wherein obtaining the range of motion capabilities from the database includes querying the database for the range of motion capability from learned range of motion capabilities.

In Example 79, the subject matter of Examples 76-78 includes, wherein obtaining the range of motion capabilities includes obtaining the range of motion capabilities from the camera by capturing a reference body part of the subject that mirrors the target body part, the reference body part performing the three-dimensional movement.

Example 80 is a system for diagnosing an issue with a target body part, the system comprising: a motion capture device to capture a series of images of three-dimensional movement of the target body part of a subject, the target body part moving relative to a reference point of the subject; a processor to: determine range of motion information for the target body part based on the captured series of images; obtain reference range of motion capabilities for the target body part; determine that the reference range of motion capabilities exceed the range of motion for the target body part; and an augmented reality device to: display, in response to the determination, using the augmented reality device, a virtual animation of the target body part, the virtual animation created using the reference range of motion capabilities and the range of motion information for the target body part.

In Example 81, the subject matter of Example 80 includes, wherein the motion capture device is one of a camera or an infrared camera.

In Example 82, the subject matter of Examples 80-81 includes, wherein to obtain the reference range of motion capabilities includes using the motion capture device to capture a reference body part of the subject that mirrors the target body part, the reference body part performing the three-dimensional movement.

In Example 83, the subject matter of Examples 80-82 includes, wherein the processor is further to determine an assessment for the target body part based on the difference set; and output the assessment for display.

In Example 84, the subject matter of Example 83 includes, wherein the assessment indicates that the target body part requires surgery.

Example 85 is at least one machine-readable medium including instructions that, when executed by processing circuitry, cause the processing circuitry to perform operations to implement of any of Examples 1-84.

Example 86 is an apparatus comprising means to implement of any of Examples 1-84.

Example 87 is a system to implement of any of Examples 1-84.

Example 88 is a method to implement of any of Examples 1-84.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method for assessing range of motion comprising:
   capturing three-dimensional data points of a target body part of a subject during motion of the target body part relative to a reference point of the subject, wherein the target body part is a first of a pair of body parts and wherein each of the pair of body parts is respectively from a different side of the subject;
   classifying the data points, including range of motion information for the target body part, as members of a movement set;
   obtaining a reference set from movement of a reference body part, to be associated with the target body part, the reference set defining range of motion capabilities for the target body part, wherein the reference set is determined based on a second set of three-dimensional data points collected from the reference body part of the subject that mirrors the target body part, wherein the reference body part is a second of the pair of body parts and is on an opposite subject side of the target body part; the reference body part having a greater range of motion than the target body part;
   computing a difference set, a member of the difference set defining a three-dimensional relationship between a member of the movement set and a corresponding member of the reference set;
   determining an assessment for the target body part based on the difference set; and
   outputting the assessment.

2. The method of claim 1, wherein the assessment indicates that the target body part requires surgery.

3. The method of claim 1, wherein outputting the assessment includes outputting the assessment to an augmented reality display for display on the augmented reality display.

4. The method of claim 1, wherein capturing the data points includes capturing sequential images using a depth camera.

5. The method of claim 1, wherein the difference set includes an angle of difference between the range of motion data of the reference set and the range of motion data of the movement set.

6. The method of claim 1, wherein capturing the data points includes capturing information at a series of points using a sensor affixed to the target body part, wherein the sensor includes an accelerometer, an inertial measurement unit (IMU), or a contact pressure sensor, and wherein the sensor is embedded in a wearable sleeve.

7. The method of claim 1, wherein the movement set includes a maximum angle of extension of the target body part and the reference set includes a maximum angle of extension for a reference body part matching the target body part, and wherein the difference set includes a difference of maximum angle of extension between the movement set and the reference set.

8. The method of claim 1, wherein the assessment is a physical therapy program including a movement challenge for the target body part.

9. The method of claim 1, wherein outputting the assessment includes:
generating a virtual component for display using the reference set;
displaying the virtual component using an augmented reality display, while permitting the target body part to be viewed through the augmented reality display;
guiding the subject, with an indication displayed on the augmented reality display, to perform movement with the target body part mimicking the virtual component.

10. The method of claim 9, wherein guiding the subject includes providing haptic feedback to the target body part with a plurality of haptic feedback devices.

11. At least one non-transitory machine-readable medium including instructions for assessing range of motion, which when executed by a machine, cause the machine to perform operations comprising:
capturing three-dimensional movement of a target body part of a subject, the target body part moving relative to a reference point of the subject, wherein the target body part is a first of a pair of body parts and wherein each of the pair of body parts is respectively from a different side of the subject;
determining performed range of motion information for the target body part based on the captured three-dimensional movement;
obtaining range of motion capabilities from movement of a reference body part, to be associated with the target body part, wherein obtaining the range of motion capabilities includes obtaining the range of motion capabilities by capturing the reference body part of the subject that mirrors the target body part, wherein the reference body part is a second of the pair of body parts and is on an opposite subject side of the target body part, the reference body part performing the three-dimensional movement;
creating a model of a three-dimensional difference between the performed range of motion and the range of motion capabilities; and
displaying, using an augmented reality device, a virtual animation of the target body part, the virtual animation created using the model of the three-dimensional difference, while permitting the target body part to be viewed through the augmented reality device.

12. The at least one machine-readable medium of claim 11, wherein obtaining the range of motion capabilities includes obtaining the range of motion capabilities from a database.

13. The at least one machine-readable medium of claim 12, wherein the operations further include training range of motion capabilities data using a machine-learning technique, and wherein obtaining the range of motion capabilities from the database includes querying the database for the range of motion capability from learned range of motion capabilities.

14. A system for assessing range of motion, the system comprising:
a motion capture device to capture a series of images of three-dimensional movement of a target body part of a subject, the target body part moving relative to a reference point of the subject, wherein the target body part is a first of a pair of body parts and wherein each of the pair of body parts is respectively from a different side of the subject;
a processor to:
determine range of motion information for the target body part based on the captured series of images;
obtain reference range of motion capabilities from movement of a reference body part, to be associated with the target body part, wherein to obtain the reference range of motion capabilities the processor is to use the motion capture device to capture the reference body part of the subject that mirrors the target body part, wherein the reference body part is a second of the pair of body parts and is on an opposite subject side of the target body part, the reference body part performing the three-dimensional movement;
determine that the reference range of motion capabilities exceed the range of motion for the target body part; and
an augmented reality device to:
display, in response to the determination, using the augmented reality device, a virtual animation of the target body part, the virtual animation created using the reference range of motion capabilities and the range of motion information for the target body part.

15. The system of claim 14, wherein the motion capture device is one of a camera or an infrared camera.

16. The system of claim 14, wherein the processor is further to:
compute a difference set, a member of the difference set defining a three-dimensional relationship between a member of the range of motion information for the target body part and a corresponding member of the reference range of motion capabilities;
determine an assessment for the target body part based on the difference set; and
output the assessment for display.

17. The system of claim 16, wherein the assessment indicates that the target body part requires surgery.

* * * * *